United States Patent [19]

Jonckers et al.

[11] Patent Number: 4,539,077
[45] Date of Patent: Sep. 3, 1985

[54] PROCESS FOR THE PREPARATION OF UREA

[75] Inventors: Kees Jonckers, Born; Petrus J. M. Van Nassau, Munstergeleen; Andreas J. Biermans, Urmond, all of Netherlands

[73] Assignee: Unie van Kunstmestfabrieken B.V., Utrecht, Netherlands

[21] Appl. No.: 487,091

[22] Filed: Apr. 21, 1983

[30] Foreign Application Priority Data

Apr. 21, 1982 [NL] Netherlands ............... 8201652

[51] Int. Cl.³ .................. B01D 3/00; B01D 5/00
[52] U.S. Cl. ............................. 203/49; 203/87; 203/91; 159/47.2; 562/555; 564/69; 564/70; 564/73
[58] Field of Search ............ 564/66, 67, 69, 68, 564/166, 70, 71, 72, 73; 203/49, 80, 87, 91; 159/47.2; 562/555

[56] References Cited

U.S. PATENT DOCUMENTS

| | | | |
|---|---|---|---|
| 2,701,262 | 2/1955 | Cook | 159/47.2 |
| 3,146,263 | 8/1964 | Otsuka | 159/47.2 |
| 3,232,982 | 2/1966 | Finneran et al. | 564/67 |
| 3,759,992 | 9/1973 | Maurovic | 564/67 |
| 4,066,693 | 1/1978 | Venderbos | 564/66 |
| 4,115,449 | 9/1978 | Biermans et al. | 564/72 |
| 4,231,839 | 11/1980 | Barron et al. | 159/47.2 |
| 8,300,862 | 3/1983 | Nassau et al. | 564/67 |

FOREIGN PATENT DOCUMENTS

| | | | |
|---|---|---|---|
| 0146752 | 3/1981 | German Democratic Rep. | 564/67 |
| 0960039 | 6/1984 | United Kingdom | 564/72 |

OTHER PUBLICATIONS

Weyermuller et al., *Dutch Urea Process*, Chemical Processing, 1962, pp. 19–22.

Primary Examiner—S. Leon Bashore
Assistant Examiner—Virginia Manoharan
Attorney, Agent, or Firm—Cushman, Darby & Cushman

[57] ABSTRACT

An improved process for the preparation of urea from carbon dioxide and excess ammonia at elevated temperature and pressure. The urea solution from the urea synthesis zone is heated and stripped at an elevated pressure to decompose a portion of the ammonium carbamate contained therein and the ammonium and carbon dioxide containing off-gas produced is condensed in a first condensation zone. The stripped urea solution is heated at a reduced pressure in a decomposition zone to decompose a further portion of ammonium carbamate, and the ammonia and carbon dioxide containing off-gas thereby produced is condensed in a second condensation zone to form an aqueous ammonium carbamate solution. A portion of this aqueous carbamate solution is introduced into a desorption zone so as to produce an off-gas more concentrated with respect to ammonia and carbon dioxide than the ammonium carbamate solution, and the off-gas from this desorption zone is condensed into a further portion of such aqueous ammonium carbamate solution in a third condensation zone, maintained at a pressure between the pressure in the decomposition zone and about 40 bar, to form a more concentrated ammonium carbamate solution which is recycled to the urea synthesis zone.

10 Claims, 2 Drawing Figures

PROCESS FOR THE PREPARATION OF UREA

BACKGROUND OF THE INVENTION

This invention relates to an improved process for the preparation of urea from ammonia and carbon dioxide.

If ammonia and carbon dioxide are introduced into a urea synthesis zone at a suitable elevated pressure (for instance 125-350 atmospheres) and temperature (for instance 170°-250° C.), ammonium carbamate is formed according to the reaction:

$$2\ NH_3 + CO_2 \rightarrow H_2N-CO-ONH_4$$

which is in turn converted into urea by dehydration according to the equilibrium reaction:

$$H_2N-CO-ONH_4 \rightleftharpoons H_2N-CO-NH_2 + H_2O.$$

The degree to which this latter conversion proceeds is dependent upon the temperature and the amount of excess ammonia and water present in the synthesis zone.

The urea synthesis effluent thereby obtained consists essentially of urea, water, nonconverted ammonium carbamate and excess ammonia. The ammonium carbamate and excess ammonia are thereupon removed from the solution and most generally they are recycled to the synthesis zone.

The synthesis zone may be a single zone in which both the ammonium carbamate and urea forming reactions proceed concurrently, or it may be divided into two separate zones for the formation, respectively, of ammonium carbamate and urea.

One process often applied for the preparation of urea is described in European Chemical News, Urea Supplement of Jan. 17, 1969, pages 17-20. In this process, the urea synthesis solution, formed at an elevated pressure and temperature, is subjected to a stripping treatment at the synthesis pressure by simultaneously heating and countercurrently contacting the solution with gaseous carbon dioxide. This results in the decomposition of a major portion of the ammonium carbamate present in the synthesis solution into ammonia and carbon dioxide, and the removal of these decomposition products from the residual urea solution as a gas mixture, together with excess ammonia, a minor quantity of water vapor, and the carbon dioxide used for stripping. This stripping treatment can be effected not only with carbon dioxide as described in the publication, but also with gaseous ammonia, an inert gas, or a mixture of any two or more of these gases (see, for instance, U.S. patent application Ser. No. 312,662 of P. Kaasenbrood).

A major portion of a gas mixture obtained in this stripping treatment is fed to a first condensation zone wherein it is condensed and absorbed into an aqueous solution originating from a subsequent treatment of the urea-containing solution. Thereafter, both the ammonium carbamate solution thus formed and the non-condensed gas mixture are recycled to the urea synthesis zone wherein the heat required for the conversion of ammonium carbamate into urea is obtained by further condensation of the gas mixture into ammonium carbamate.

The product urea solution from the stripping zone, still containing residual ammonium carbamate, is subsequently expanded to a low pressure (for instance 3-6 bar) and heated by means of steam so as to decompose a further amount of ammonium carbamate and remove the decomposition products, together with an amount of water vapor. The gas mixture obtained from this ammonium carbamate decomposition zone is condensed in a second condensation zone operated at a relatively low pressure wherein it is absorbed into an aqueous solution absorption agent to form a dilute ammonium carbamate solution. This dilute ammonium carbamate solution is pumped back up to the pressure of the high-pressure part of the urea synthesis and ultimately recycled into the urea synthesis zone.

The remaining product urea solution removed from the decomposition zone is further reduced in pressured and worked up to a concentrated aqueous urea solution, or it is further processed into solid urea. In so doing, water is removed from the urea solution by evaporation, and the urea melt thus obtained is processed into granules, or the concentrated urea solution is crystallized. The gases obtained from this evaporation or crystallization step contain, in addition to water vapor, an amount of ammonia, carbon dioxide, and entrained urea droplets, all of which is condensed to form process condensate. A portion of this process condensate is used as the aqueous absorption agent for the gas mixture condensed in the second condensation zone. A remaining portion of this process condensate can be treated with high-pressure steam so as to decompose or hydrolyze the urea present into ammonia and carbon dioxide, and to recover the decomposition products, together with the ammonia and carbon dioxide present in the process condensate, by means, for instance, as described in Industrial Wastes, September/October, 1976, pages 44-47.

Inasmuch as the conversion of ammonium carbamate into urea in the urea synthesis zone is an equilibrium reaction in which water is formed, the amount of water recycled, and thus present in the synthesis zone, should be as small as possible. Therefore, it is advantageous to have the recycled ammonium carbamate solution as concentrated as possible. However, to prevent the formation of solid ammonium carbamate in the recycled solution, a certain minimum amount of water must be present, depending upon the temperature, and thus the pressure. This minimum amount of water required in the carbamate solution decreases with increasing temperature, and thus with increasing pressure.

Thus, it is inevitable that some amount of water is introduced into the synthesis zone with the carbamate solution formed in the second condensation zone, which is supplied to the synthesis zone via, for instance, the first condensation zone, which adversely effects the efficiency of the conversion of ammonium carbamate into urea.

BRIEF DESCRIPTION OF THE INVENTION

An object of the present invention is to provide an improved process in which the amount of water ultimately supplied to the urea synthesis can be reduced without incurring the risk of forming solid ammonium carbamate in the recycle stream.

In accordance with the invention, the ammonium carbamate solution that is recycled to the urea synthesis zone is further processed in a manner whereby it is concentrated, thus having a lower water content. The present invention is, therefore, an improvement to a process for the preparation of urea wherein ammonia and carbon dioxide are reacted at elevated temperature and pressure in a urea synthesis zone to form an aqueous urea synthesis solution containing product urea, ammonium carbamate, and excess ammonia. This synthesis solution is introduced into a stripping zone wherein it is simultaneously heated and stripped at an elevated pressure with a stripping gas to decompose ammonium carbamate, and to remove the ammonia and carbon dioxide thus formed, together with the excess ammonia. The stripping gas used in the stripping zone may be carbon dioxide, ammonia, inert gas, or mixtures of any two or more of these gases.

The stripping zone off-gas, containing ammonia, carbon dioxide and water vapor, in addition to the stripping gas introduced, is condensed in a first condensation zone to form a first ammonium carbamate solution. The stripped urea solution leaving the stripping zone, still containing an amount of ammonium carbamate, is reduced in pressure and introduced into a decomposition zone wherein a further portion of ammonium carbamate is decomposed, and a decomposition zone off-gas containing ammonia, carbon dioxide, and water vapor is separated from the remaining product urea solution. This decomposition zone off-gas is then condensed in a second condensation zone to form a second ammonium carbamate solution.

In accordance with the improvement of the invention, a portion of the second ammonium carbamate solution is introduced into a desorption zone wherein a concentrated off-gas containing ammonia and carbon dioxide, having relatively little water vapor, is removed from the residual liquid phase. The desorption zone will preferably have a pressure greater than the pressure in said decomposition zone, i.e. between the pressure in the decomposition zone and about 40 bar, and most preferably between 10 and 25 bar. This desorption zone off-gas is more concentrated with respect to ammonia and carbon dioxide than the second ammonium carbamate solution, and is condensed in a third condensation zone into a further portion of the second ammonium carbamate solution so as to form a more concentrated aqueous solution of ammonium carbamate. The more concentrated solution of ammonium carbamate thus obtained is ultimately recycled to the urea synthesis zone.

The pressures in the synthesis zone, the stripping zone, and the first condensation zone may be either the same or different. However, it is of advantage to maintain the pressure in the first condensation zone equal to that in the urea synthesis zone. This makes it possible to condense only a portion of the gas mixture in the first condensation zone, and to introduce a sufficient amount of non-condensed gases, together with the condensed ammonium carbamate solution, into the urea synthesis zone that the condensation of these gases will provide the heat required for the endothermic urea formation reaction to proceed. Moreover, steam of maximum pressure can then be formed by using the heat of condensation, absorption, and carbamate formation liberated at the higher pressure and temperature in the first condensation zone.

The formation of ammonium carbamate in the third condensation zone is effected at a pressure between the pressure in the decomposition zone and about 40 bar. Preferably, this third condensation zone will be maintained at a pressure of between about 10 and 25 bar because in this range, compared to the relatively lower pressure in the second condensation zone, the amount of water required to avoid crystallization in the ammonium carbamate solution is already significantly reduced. Pressures exceeding 40 bar may be used, but the formation of ammonium carbamate solutions at these higher pressures requires a larger investment in processing equipment, and expensive high-pressure steam. Above this level, the resulting higher costs are greater than the savings realized from the additional urea yield obtained due to increased conversion efficiency in the urea synthesis zone.

In a preferred embodiment, the stripped urea solution from the stripping zone is expanded to a pressure no lower than the pressure in the third condensation zone, and the gas mixture thus released is separated from the remaining urea solution. The gas mixture formed in this separation, which consists primarily of ammonia and carbon dioxide, and contains significantly less water than the liquid phase that is in equilibrium with it, is then fed to the third condensation zone. The remaining urea solution is then introduced into the decomposition zone for the removal of a further amount of ammonium carbamate.

In accordance with the improvement of this invention, the desorption zone into which a portion of the second ammonium carbamate solution is introduced can advantageously be a distillation column wherein a relatively concentrated gas mixture containing ammonia and carbon dioxide with little water vapor can be removed from the residual liquid phase. It may be more advantageous, however, to form this concentrated gas mixture with low water content by treating this portion of the second ammonium carbamate solution with a stripping gas. Suitable stripping gases are ammonia, carbon dioxide, and particularly steam. Although it is possible to use other stripping gases, these have the disadvantage that they must be separated off later by laboreous procedures.

In a particularly preferred embodiment, the formation of the more concentrated ammonia and carbon dioxide gas mixture in the desorption zone is carried out in conjunction with the hydrolysis of urea that is present in process condensate produced in the further processing of the urea solution by evaporation and/or crystallization. In carrying out this urea hydrolysis treatment of the process condensate, the major portion of ammonia and carbon dioxide are preferably first removed by stripping the process condensate at a relatively low pressure. Thereafter, in a reaction column, high pressure steam is passed cocurrently or countercurrently to the process condensate to serve as both a heating agent, to accomplish the urea hydrolysis, and as a stripping agent, to remove the ammonia and carbon dioxide thus released.

A process of this type, in which the process condensate and steam are passed countercurrently through the reaction column, is described in copending application No. 325,922 filed Nov. 30, 1981, the disclosure of which is hereby incorporated by reference. In the process disclosed in that application, steam containing ammonia and carbon dioxide is discharged from the top of the reaction column at a pressure of 10–30 bar, from which the ammonia and carbon dioxide are subsequently recovered.

In accordance with this preferred embodiment of the present invention, the steam discharged from the top of the reaction column used for the hydrolysis and stripping of the process condensate can be effectively utilized to concentrate the ammonium carbamate solution from the second condensation zone. Thus, a portion of the solution from the second condensation zone is brought up to the pressure of the third condensation zone, or higher if desired, and introduced into the desorption zone wherein it is countercurrently contacted with the ammonia and carbon-dioxide containing steam from the top of the reaction column. If necessary, the desorption zone can also be provided with a reboiler, or additional high-pressure steam can be supplied.

When operating in accordance with this preferred embodiment, the major portion of the ammonium carbamate in the ammonium carbamate solution introduced into the desorption zone from the second condensation zone is decomposed into ammonia and carbon dioxide, and most of the entrained water vapor is condensed, resulting in the formation of an ammonia and carbon dioxide containing desorption zone off-gas having a relatively low water vapor content. This concentrated gas mixture is then sent to the third condensation zone wherein it is condensed into a further portion of ammonium carbamate solution from the second condensation zone and ultimately recycled back to the urea synthesis reactor. The desorption zone should be provided with facilities to effect good contact between the gas and liquid. This desorption zone can be accommodated either in separate apparatus or in the upper portion of the reaction column used for hydrolysing the urea in the process condensate.

Preferably, the pressure in the reaction column and in the desorption zone are at least equal to the pressure in the third condensation zone so that no additional compression energy is required to supply the desorption zone off-gas to the third condensation zone.

The water content of the ammonium carbamate solution formed in the third condensation zone may be further controlled according to the invention by increasing or decreasing the amount of carbamate solution that is fed directly from the second condensation zone into the third condensation zone. The amount of condensate from the second condensation zone fed directly to the third condensation zone is preferably controlled so as to maintain a minimum water content as necessary to prevent the crystallization of the concentrated ammonium carbamate solution thus formed. This minimum water content depends upon the pressure and associated temperature conditions chosen.

When operating in accordance with the improvement of the present invention, it is possible to appreciably reduce the amount of water that is supplied to the high-pressure portion of the urea synthesis process and introduced into the urea synthesis zone, with the effect of allowing a higher conversion efficiency to be reached in the synthesis zone. As a result, the urea synthesis effluent contains a smaller amount of ammonium carbamate to be decomposed in the stripping zone, so that less high pressure steam is required in the stripping zone. This also increases the stripping efficiency in this stripping zone. Moreover, since less water is required for the formation of the carbamate solution in the third condensation zone, less water will be carried along with the urea product stream so that less low-pressure steam is required for its further processing, and the equipment required for this further processing, such as evaporators and crystallizers, can be smaller, resulting in a further investment cost savings. Furthermore, the ammonium carbamate pump used to recycle the ammonium carbamate solution to the high-pressure part of the urea synthesis can be of a smaller capacity.

On the other hand, an additional ammonium carbamate condensation zone, a desorption zone, a carbamate pump for transporting the carbamate solution from the second condensation zone to the third condensation zone, and possibly also an expansion vessel, must be installed to practice the improvement of the invention. However, the reduction in the amount of high pressure steam required is quite appreciable, and may amount to a savings of approximately 85–135 tons of steam per day for a production unit having a capacity of 1500 tons of urea per day, when the pressure in the third condensation zone is, for instance, in the range of about 18–25 bar. This saving amply outweighs the extra investment required for the additional equipment necessary for effecting this process.

DETAILED DESCRIPTION OF THE INVENTION

The improvement of the present invention will be discussed in greater detail in terms of the specific embodiments illustrated in the figures.

Figure 1:
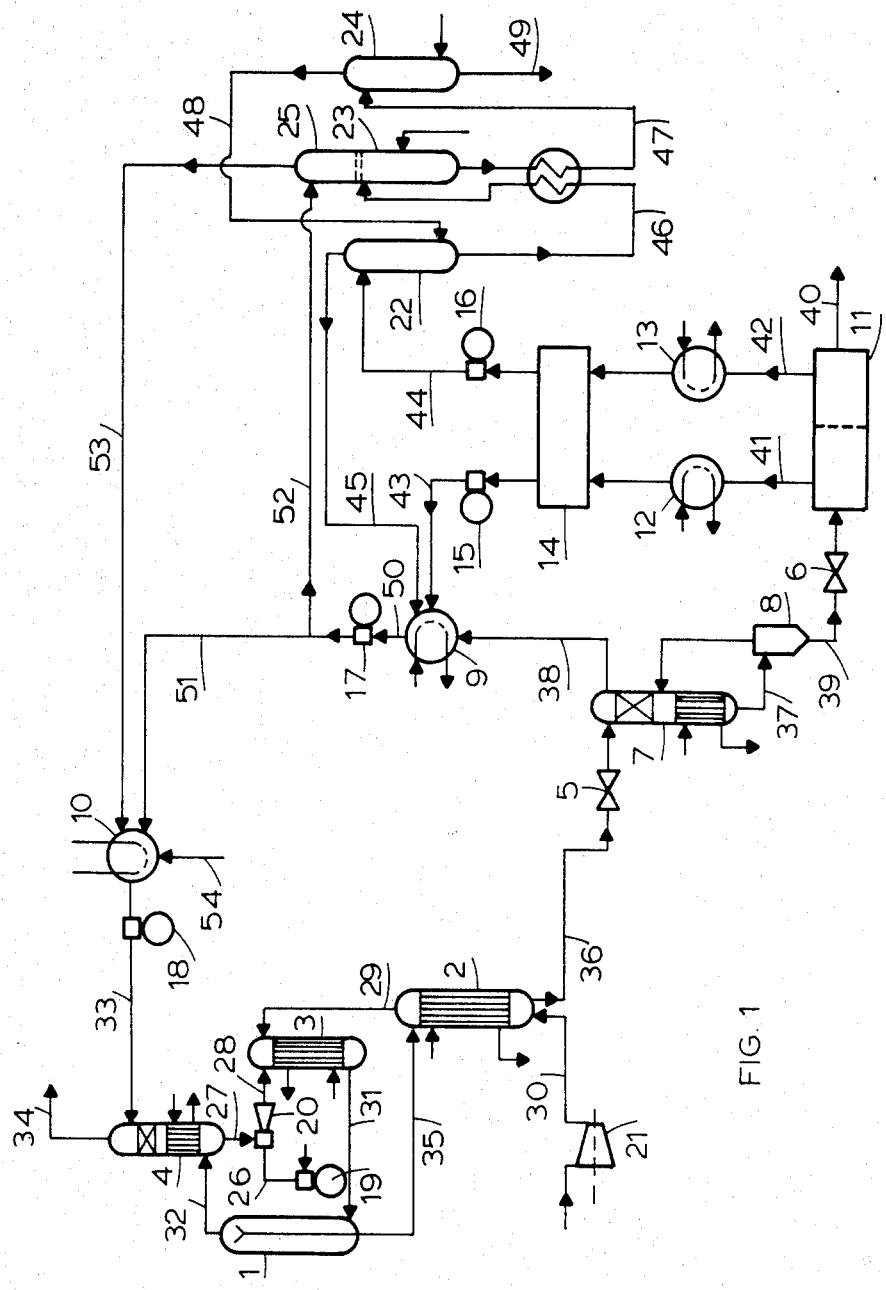
FIG. 1 diagramatically illustrates an embodiment of the present invention in which the stripped urea synthesis solution is expanded to the pressure of the second condensation zone in one step.

In the embodiment according to FIG. 1, the high pressure part of the process, which may be operated at a pressure of, for instance, 125–350 bar, is comprised of synthesis zone 1, stripping zone 2, first condensation zone 3, and washing column 4. The expansion valves for the urea product stream are represented by 5 and 6, the decomposition zone by 7, a gas-liquid separator by 8, the second condensation zone by 9, and the third condensation zone by 10. A two-step evaporation section is illustrated as 11, condensers as 12 and 13, a process condensate tank as 14, process condensate pumps as 15 and 16, carbamate solution pumps as 17 and 18, an ammonia pump as 19, an ejector as 20, and a carbon dioxide compressor as 21.

The process condensate is worked up in predesorption zone 22, hydrolysis zone 23, and final desorption zone 24. Hydrolysis zone 23 is provided with a desorption zone 25 for the formation of the gas mixture, having low water content, from a portion of the condensate from the second condensation zone in accordance with the improvement of the invention.

In first condensation zone 3, recycle and fresh ammonia and carbon dioxide containing feeds are partially condensed to ammonium carbamate, and the carbamate solution thus formed, together with the non-condensed gas mixture, is supplied to urea synthesis zone 1 via line 31. In synthesis zone 1, the further condensation of this non-condensed ammonia and carbon dioxide to ammonium carbamate develops sufficient heat to meet the heat requirements of the endothermic conversion of ammonium carbamate into urea. The resulting urea synthesis effluent is discharged from the synthesis zone and introduced into stripping zone 2 via line 35. A portion of the gas mixture that is not condensed in the synthesis zone, containing the inert gases introduced into the process with the fresh ammonia and carbon dioxide and possibly as passivation air or oxygen, is supplied via line 32 to washing column 4 wherein the inerts are freed of ammonia and carbon dioxide by washing with recycle ammonium carbamate introduced via line 33, and the inerts are discharged from the process via line 34.

Recycle ammonium carbamate solution is withdrawn from washing column 4 by ejector 20, which is driven by liquid ammonia introduced into the process via ammonia pump 19 and line 26, and both the ammonium carbamate and ammonia are fed into first condensation zone 3 via line 28. The gas mixture from stripping zone 2 is also sent to first condensation zone 3 via line 29. This latter gas mixture is obtained from the stripping of the urea synthesis solution introduced into stripping zone 2 via line 35.

In stripping zone 2, this urea synthesis solution is simultaneously heated and passed countercurrently to a carbon dioxide stripping gas which has been compressed by carbon dioxide compressor 21 and introduced into the bottom of the stripping zone via line 30. Stripping zone 2 may be designed as a vertical tubular heat exchanger wherein the heat required for stripping is supplied in the form of high-pressure steam of, for instance, 15–30 bar.

In first condensation zone 3, a portion of the ammonia and carbon dioxide introduced via lines 28 and 29 is condensed to ammonium carbamate. This first condensation zone may, for instance, be designed as a vertical tubular heat exchanger, and the heat liberated in the exothermic condensation to form ammonium carbamate can be discharged with the aid of boiler feed water which can thereby be converted into low-pressure steam of 4–5 bar. This ammonium carbamate solution thus formed, together with the non-condensed gas, are supplied to the synthesis zone via line 31.

The stripped urea synthesis solution from stripping zone 2 is passed via line 36 through expansion valve 5, wherein its pressure is decreased to, for instance, 2–3 bar, and fed into decomposition zone 7, which is provided with a gas-liquid separator 8. This decomposition zone 7 may be designed, for instance, as a vertical tubular heat exchanger with a rectification portion provided at the top. In this zone, the stripped urea synthesis solution is heated with low-pressure steam of 2–3 bar, and a major portion of the ammonium carbamate still present in the solution is decomposed, and the reaction mixture thus formed flows via line 37 to gas-liquid separator 8. In gas-liquid separator 8, a gas phase of ammonia, carbon dioxide, and water vapor is separated from the residual urea product solution and returned to the rectification portion of decomposition zone 7, wherein the water content of the gas phase formed by the heating is reduced. Additionally, the gas phase which spontaneously formed upon expansion of the stripped urea synthesis solution, comprised of ammonia, carbon dioxide, and water vapor, is separated off in the top of this zone and led, together with the gas phase formed by the heating, to second condensation zone 9 via line 38, wherein it is condensed to form an aqueous solution of ammonium carbamate. This second condensation zone 9 can also be designed as a vertical tubular heat exchanger in which the heat liberated can be discharged with the aid of cooling water.

The residual urea product stream obtained in gas-liquid separator 8 is passed via line 39 through expansion valve 6, whereby the solution is expanded to atmospheric pressure or below. The expanded solution is then introduced into evaporation section 11, which is here illustrated as consisting of two stages. The concentrated product urea solution formed in evaporation section 11 is discharged via line 40. Water vapor formed during evaporation, which contains a slight amount of ammonia and carbon dioxide, as well as decomposition products of urea and entrained urea droplets, is passed via lines 41 and 42, respectively, to coolers 12 and 13, respectively, where it is condensed by means of cooling water. The process condensate thus formed is collected in process condensate collecting tank 14. A small amount of this process condensate is transported from collecting tank 14 via condensate pump 15 and line 43 to second condensation zone 9, wherein it is used as an absorption agent for the gas mixture supplied to this condensation zone.

A major portion of the process condensate is pumped by means of condensate pump 16 via line 44 to apparatus for processing the process condensate, which is made up of pre-desorption zone 22, hydrolysis zone 23, and final desorption zone 24.

In pre-desorption zone 22, ammonia and carbon dioxide present in the process condensate are removed at a pressure of 1–5 bar by stripping with the water-rich gas mixture introduced via line 48 from final desorption zone 24. The off-gas thus obtained is discharged from pre-desorption zone 22 and introduced into second condensation zone 9 via line 45. The process condensate stripped in pre-desorption zone 22 is pumped via line 46 into hydrolysis zone 23 wherein it is treated countercurrently with high-pressure steam of, for instance, 15–42 bar. This steam treatment results in hydrolysis of the urea, and the removal of the ammonia and carbon dioxide thus formed by means of the stripping action of the steam. The gas mixture thus formed, comprised of carbon dioxide and ammonia containing steam, is introduced into desorption zone 25, placed above the hydrolysis zone, wherein it is used as a stripping gas.

The aqueous solution discharged from the bottom of hydrolysis zone 23 is first used to heat the liquid feed to the hydrolysis zone from pre-desorption zone 22, and is introduced via line 47 into final desorption zone 24 wherein ammonia and carbon dioxide still present in the liquid are removed at a pressure of 1–5 bar by stripping with low-pressure steam. The gas mixture obtained in final desorption zone 24 is sent to pre-desorption zone 22 via line 48, and the residual liquid stream, now essentially free of urea, ammonia, and carbon dioxide, is discharged from the process via line 49.

The ammonium carbamate solution forme in second condensation zone 9, which contains approximately 32–36 weight percent water, is discharged from this zone via line 50 and increased to a pressure of, for instance, 10–25 bar by means of pump 17. A portion of this ammonium carbamate solution is sent via line 51 directly to third condensation zone 10, which is operated at essentially the same pressure. The remaining portion of the ammonium carbamate solution from second condensation zone 9 is passed, via line 52, to the top of desorption zone 25 which is provided with means to effect a good contact between liquid and gas. In desorption zone 25, the ammonium carbamate solution is passed countercurrently against the ammonia and carbon dioxide containing steam from hydrolysis zone 23 whereby the heat content and the stripping action of the steam decompose the ammonium carbamate and the steam condenses, and the ammonia and carbon dioxide formed, together with the ammonia and carbon dioxide present in the steam, are discharged from the top of zone 25 with only a small amount of water vapor. The remaining aqueous liquid flows into the top of hydrolysis zone 23 and is processed together with the liquid supplied via line 46.

The gas mixture containing ammonia and carbon dioxide having low water vapor content that is obtained in desorption zone 25 is passed, via line 53, to third condensation zone 10 where it is condensed into a portion of the ammonium carbamate solution fed directly from the second condensation zone. The relative amounts of ammonium carbamate solution supplied via line 51 and gas mixture of low water vapor content supplied via line 53, are chosen in such a proportion that the ammonium carbamate solution formed in third condensation zone 10 contains only a little water in excess of that amount needed to prevent crystallization of ammonium carbamate. If desired, liquid ammonia can also be supplied to third condensation zone 10 via line 54 to ensure that at the prevailing pressure the maximum condensation temperature is obtained and a minimum amount of water is required.

Preferably, the pressure in third condensation zone 10 is chosen so that it is no higher than the pressure maintained in desorption zone 25, so that no compression of the gas mixture supplied from zone 25 via line 53 is necessary. Third condensation zone 10 can advantageously be designed as a vertical tubular heat exchanger, and the heat developed in the carbamate formation in this zone can be utilized for heating the ammonia or process flows as required for the urea preparation.

The ammonium carbamate solution obtained in third condensation zone 10 is brought up to the pressure prevailing the high pressure portion of the process by means of carbamate pump 18 and is recycled to the urea synthesis zone. In the embodiment illustrated, this recycle is first supplied to washing column 4 via line 33. However, it is also possible to feed this ammonium carbamate solution directly to urea synthesis zone 1 or first condensation zone 3.

The water content of this ammonium carbamate solution formed in third condensation zone 10 depends upon the pressure maintained in this zone, but will generally be in the range of between about 10 and 30 percent by weight. This contrasts to the water content in the ammonium carbamate solution obtained in second condensation zone 9 of between about 32 and 36 percent by weight, and thus constitutes a very significant reduction, resulting in a higher degree of conversion in the urea synthesis zone.

Figure 2:
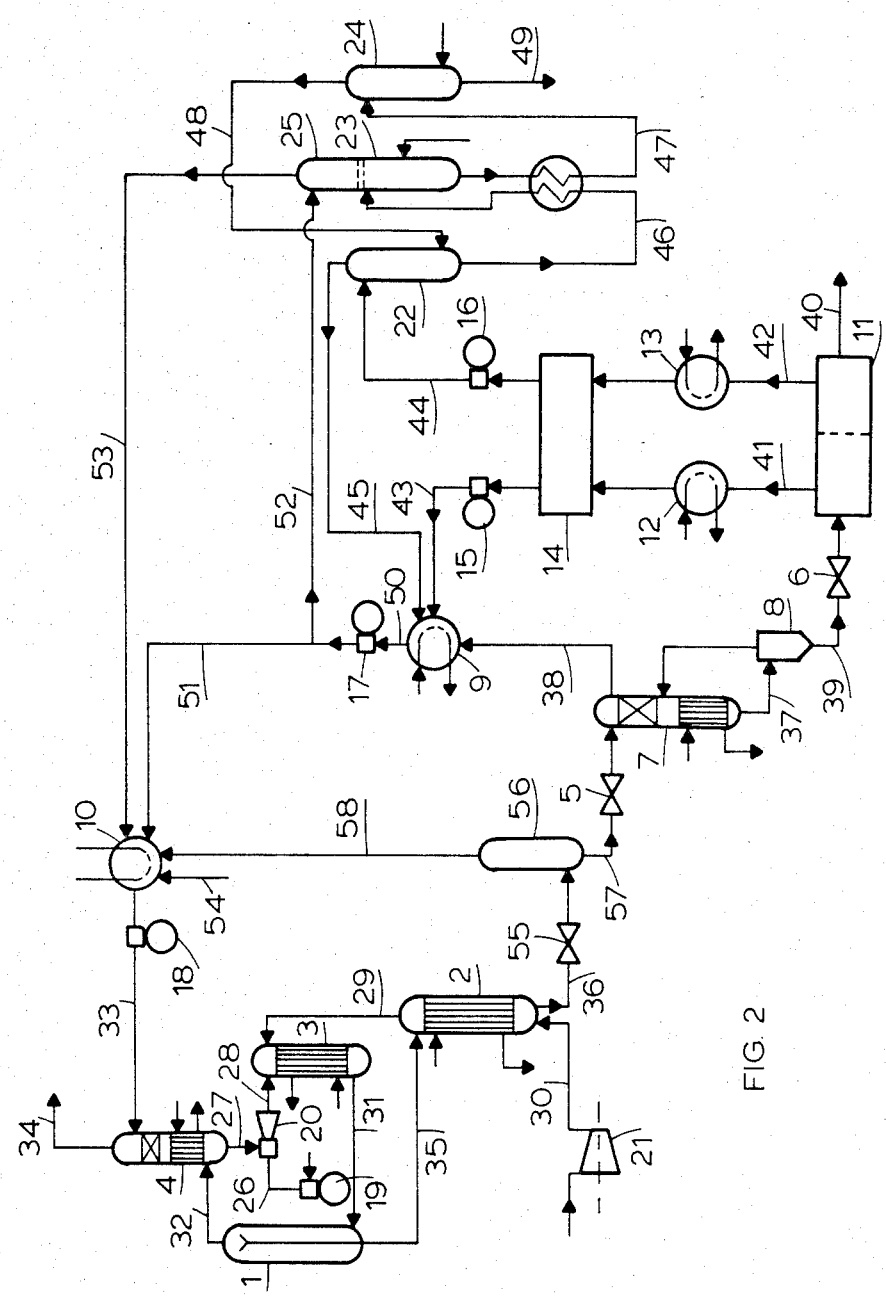
FIG. 2 diagramatically illustrates another embodiment of the invention in which the stripped urea synthesis solution is expanded to the pressure of the second condensation zone in two steps, with the separate removal of an off-gas at the intermediate pressure level.

In the embodiment of the process illustrated in FIG. 2, the stripped urea synthesis solution discharged from stripping zone 2 via line 36 is first expanded to the pressure of the third condensation zone, for instance 18 bar, by means of expansion valve 55 and expansion vessel 56 wherein the gas phase spontaneously evolved is separated from the residual urea product stream. The residual urea product stream obtained in expansion vessel 55 is further expanded through expansion valve 5 and led to decomposition zone 7 via line 57.

The gas phase separated in expansion vessel 56, which has a water content considerably lower than the liquid phase with which it is in equilibrium, is led to third condensation zone 10 via line 58. As a result, the amount of gas mixture to be supplied to second condensation zone 9 via line 38 becomes smaller, with the result that the amount of process condensate via line 43 required for effecting complete absorption of the gas mixture supplied to second condensation zone 9 can be smaller, with the consequence that the apparatus constituting the second condensation zone can be smaller.

Inasmuch as the gas mixture supplied to third condensation zone 10 from expansion vessel 56 via line 58 contains little water, a smaller amount of gas mixture treated in desorption zone 25 and supplied via line 53 is sufficient to obtain the desired low water content in third condensation zone 10. Accordingly, the amount of ammonium carbamate solution from condensation zone 9 treated in desorption zone 25 can be descreased with the result that the apparatus constituting desorption zone 25 can be of smaller dimensions.

EXAMPLE I

Using the process described above, urea was prepared according to the embodiment illustrated in FIG. 1 in a plant having a production capacity of 1500 tons a day. All flow quantities indicated below are in kg per hour. The pressures maintained in the high pressure portion of the plant, including synthesis zone 1, stripping zone 2, first condensation zone 3, and washing column 4 was 140 bar. The pressure in second condensation zone 9 was 3 bar and the pressure in third condensation zone 10 was 18 bar.

By means of ammonia pump 19, 34,382 kg liquid $NH_3$, having a temperature of 81° C., was supplied to first condensation zone 3 of the high-pressure part of the plant. Using carbamate pump 18, a carbamate solution from third condensation zone 10, which contained 8,318 kg $NH_3$, 9,359 kg $CO_2$, and 4,783 kg $H_2O$, was supplied to first condensation zone 3 via washing column 4 in which a further amount of 9,421.4 kg $NH_3$, 8,615.2 kg $CO_2$ and 439.2 kg $H_2O$ was absorbed in the solution, with the aid of ejector 20. By means of carbon dioxide compressor 21, 47,987 kg $CO_2$ was compressed and introduced into the bottom of stripping zone 2 at a temperature of 100° C. Urea synthesis solution coming from the synthesis zone at a temperature of 183° C., containing 65,556 kg urea, and 49,207 kg $NH_3$, 30,351 kg $CO_2$ and 26,883 kg water as ammonium carbamate and excess ammonia was also introduced into stripping zone 2. As a result of the heat supplied to the stripping zone and the stripping effect of the $CO_2$, a major portion of the carbamate present in the synthesis solution was decomposed in this stripping zone.

From stripping zone 2 a gas stream consisting of 43,619 kg $NH_3$, 69,000 kg $CO_2$, and 3,437 kg water was passed to first condensation zone 3 and for the most part condensed there. From condensation zone 3 the carbamate solution formed by the condensation reaction and the noncondensed gases were passed to synthesis zone 1. The stripped urea synthesis solution obtained from stripping zone 2, in addition to 64,404 kg urea, contained 6,239 kg $NH_3$, 8,074 kg $CO_2$, and 24,300 kg water. The pressure of this solution was subsequently reduced to 3 bar by means of expansion valve 5, after which the solution was passed to decomposition zone 7, provided with gas-liquid separator 8, where most of the ammonium carbamate still present in the stripped urea solution was decomposed and the gas mixture formed was separated from the solution. In decomposition zone 7, steam of 4.5 bar was applied as the heating medium.

The gas mixture removed from the top of the decomposition zone, including that obtained in the gas-liquid separator, totaling 14,470 kg and consisting of 4,767 kg $NH_3$, 7,405 kg $CO_2$, and 2,298 kg water, was passed to second condensation zone 9, where it was condensed at a pressure of 3 bar. Also supplied to second condensation zone 9, via line 45, was the gas mixture obtained by desorption of the $NH_3$ and $CO_2$ from the process condensate in predesorption zone 22 prior to the urea hydrolysis. This gas mixture consisted of 2,246 kg $NH_3$, 1,795 kg $CO_2$, and 2,695 kg water. To insure complete absorption of the gas mixtures in second condensation zone 9, 3,660 kg process condensate, containing 221 kg $NH_3$, 158 kg $CO_2$, and 102 kg urea, was supplied to this zone. The heat liberated by this condensation was discharged by means of cooling water, and 24,866 kg of carbamate solution was obtained, having a temperature of 75° C. and containing 32.9 wt. % water. This ammonium carbamate solution was subsequently brought to a pressure of 18 bar by means of pump 17.

In desorption zone 25, 12,851 kg of the carbamate solution from second condensation zone 9 was passed countercurrently to the high-pressure steam from the hydrolysis of the urea present in the process condensate. This yielded 9,462 kg of a gas mixture containing 3,754 kg $NH_3$, 4,858 kg $CO_2$, and 850 kg water, and having a temperature of 141° C.

This gas mixture, and the remaining 12,015 kg of carbamate solution from second condensation zone 9, were passed to third condensation zone 10, which was maintained at a pressure of 18 bar. In addition, 1,085 kg liquid $NH_3$, having a temperature of 15° C., was pumped into this zone. The heat liberated during this carbamate formation was utilized for preheating the liquid $NH_3$ required for the urea synthesis. The carbamate solution obtained in third condensation zone 10, which totaled 22,561 kg and contained only 21.1% water, was pumped back to washing column 4 of the high-pressure part of the plant.

The high-pressure steam consumption, including that for driving the $CO_2$ compressor, was 1,205 kg steam of 40 bar per ton urea. Without application of the measures according to the invention the carbamate solution to be recycled would contain 32.9 wt. % water and the consumption of high-pressure steam would amount to 1,264 kg of 40 bar per ton urea.

EXAMPLE II

According to the embodiment illustrated in FIG. 2, urea was prepared in a plant having a production capacity of 1500 tons a day. The stripped urea synthesis solution discharged from stripping zone 2 was first expanded, by means of expansion valve 55 and expansion vessel 56 to a pressure of 18 bar, and the gas phase formed by this expansion was separated and supplied directly to third condensation zone 10, which was also maintained at a pressure of 18 bar. The liquid phase formed in expansion vessel 56 was further reduced in pressure to 3 bar by means of expansion valve 5 and the gas-liquid mixture thus obtained was processed as described in Example I.

The stripped urea synthesis solution, totaling 103,029 kg, consisted of 64,404 kg urea, 6,239 kg $NH_3$, 8,074 kg $CO_2$, and 24,312 kg water. Upon expansion to 18 bar in expansion vessel 56, a gas mixture with a temperature of 155° C. was obtained, in total 2,474 kg, consisting of 247 kg $NH_3$, 2,116 kg $CO_2$, and 111 kg water. This gas mixture was passed to third condensation zone 10.

The remaining liquid phase from expansion vessel 56, in total 100,555 kg, consisting of 64,404 kg urea, 5,994 kg $NH_3$, 5,957 kg $CO_2$, and 24,200 kg water, was reduced in pressure to 3 bar and introduced into decomposition zone 7, provided with gas-liquid separator 8, wherefrom a gas mixture was separated which contained 4,520 kg $NH_3$, 5,289 kg $CO_2$, and 1,978 kg water. This gas mixture was introduced in second condensation zone 9, together with 6,039 kg of a gas mixture obtained by the desorption of $NH_3$ and $CO_2$ from the process condensate in predesorption zone 22, consisting of 2,207 kg $NH_3$, 1,417 kg $CO_2$, and 2,415 kg water. In addition, 3,110 kg process condensate, containing 102 kg urea, 185 kg $NH_3$, and 132 kg $CO_2$, was introduced into second condensation zone 9 via line 43. An amount of 20,935 kg ammonium carbamate solution was obtained, which had a temperature of 75.2° C. and which contained 33.8 wt. % water.

In desorption zone 25, 9,563 kg of the ammonium carbamate solution from the second carbamate condenser was stripped in desorption zone 25 at a pressure of 18 bar, by means of steam from the hydrolysis treatment of the urea present in the process condensate. The resulting gas mixture, in total 7,630 kg, contained 3,247 kg $NH_3$, 3,542 kg $CO_2$, and 841 kg water and had a temperature of 141° C. This gas mixture was condensed in the remaining 11,372 kg of carbamate solution from the second condensation zone in third condensation zone 10, to which 1,085 kg liquid $NH_3$ with a temperature of 15° C. was also supplied.

In the third condensation zone, 22,561 kg of carbamate solution was obtained, which contained 21.2 wt. % water. The consumption of high-pressure steam, including that for driving the $CO_2$ compressor, was 1,174 kg steam of 40 bar.

What is claimed is:

1. In a process for the preparation of urea from carbon dioxide and an excess of ammonia at an elevated temperature and pressure in a urea synthesis zone to form an aqueous urea synthesis solution containing urea, ammonium carbamate, and excess ammonia, and thereafter:

heating and stripping said urea synthesis solution in a stripping zone at an elevated pressure with a first stripping gas selected from the group consisting of carbon dioxide, ammonia, inert gas, and mixtures thereof, thereby decomposing ammonium carbamate and separately removing a stripping zone off-gas containing ammonia, carbon dioxide, and water vapor from a first urea solution still containing residual ammonium carbamate;

at least partially condensing said stripping zone off-gas in a first condensation zone to form a first ammonium carbamate solution;

introducing said first urea solution into a decomposition zone at reduced pressure relative to said stripping zone wherein a further portion of ammonium carbamate is decomposed and separately removing a decomposition zone off-gas containing ammonia, carbon dioxide, and water vapor, from a second urea solution;

further processing said second urea solution in a further processing zone to form a concentrated urea solution or solid urea product; and condensing said decomposition zone off-gas in a second condensation zone to form a second ammonium carbamate solution;

the improvement comprising:

introducing a portion of said second ammonium carbamate solution into a desorption zone maintained at a pressure of between about 2 and 40 bar wherein a desorption zone off-gas more concentrated with respect to ammonia and carbon dioxide than said second ammonium carbamate solution is separately removed from a residual liquid phase;

condensing said desorption zone off-gas into a further portion of said second ammonium carbamate solution in a third condensation zone maintained at a pressure between about 2 and 40 bar to form a concentrated third aqueous ammonium carbamate solution; and recycling said third ammonium carbamate solution to said urea synthesis zone.

2. The process of claim 1 wherein said first ammonium carbamate solution is recycled to said urea synthesis zone.

3. The process of claim 2 wherein said third ammonium carbamate solution is introduced into said first condensation zone and recycled to said urea synthesis zone together with said first ammonium carbamate solution.

4. The process of claim 1 wherein said first urea solution from said stripping zone, before being introduced into said decomposition zone, is expanded, thereby decomposing a portion of said residual ammonium carbamate into ammonia and carbon dioxide, and introducing the gas mixture thus produced into said third condensation zone.

5. The process of claim 1 wherein said desorption zone and said third condensation zone are maintained at a pressure of between about 10 and 25 bar.

6. The process of claim 1 wherein said desorption zone off-gas is formed in said desorption zone by distillation of said portion of the second ammonium carbamate solution.

7. The process of claim 1 wherein the desorption zone off-gas is formed in said desorption zone by stripping said portion of the second ammonium carbamate solution with a second stripping gas.

8. The process of claim 7 wherein the second urea solution is further processed in said further processing zone by means of evaporation or crystallization thereby resulting in the formation of a vapor phase which is condensed to form process condensate containing ammonia, carbon dioxide and urea, and the urea present in said process condensate is removed by hydrolysis in a hydrolysis zone thereby forming a hydrolysis zone off-gas, and wherein said hydrolysis zone off-gas is used as said second stripping gas.

9. The process of claim 8 wherein the pressure in said third condensation zone is less than or equal to the pressure in said hydrolysis zone.

10. The process of claim 1 wherein the water content of said concentrated ammonium carbamate solution recycled from said third condensation zone is controlled by regulation of the proportion of ammonium carbamate solution from said second condensation zone that is supplied directly to said third condensation zone.

* * * * *